US010105035B2

(12) United States Patent
Gafford et al.

(10) Patent No.: US 10,105,035 B2
(45) Date of Patent: Oct. 23, 2018

(54) MODULAR, MILLIMETER-SCALE, LIGHT-INTENSITY-BASED FORCE SENSING SYSTEM

(71) Applicant: President and Fellows of Harvard College, Cambridge, MA (US)

(72) Inventors: Joshua Gafford, Somerville, MA (US); Conor J. Walsh, Cambridge, MA (US); Robert J. Wood, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 335 days.

(21) Appl. No.: 15/183,501

(22) Filed: Jun. 15, 2016

(65) Prior Publication Data

US 2017/0360279 A1 Dec. 21, 2017

(51) Int. Cl.
*G01B 11/16* (2006.01)
*A61B 1/00* (2006.01)
(Continued)

(52) U.S. Cl.
CPC .......... *A61B 1/00096* (2013.01); *A61B 1/005* (2013.01); *A61B 1/0676* (2013.01);
(Continued)

(58) Field of Classification Search
CPC ............................. G01J 3/0202; G01J 3/4535
See application file for complete search history.

(56) References Cited

U.S. PATENT DOCUMENTS 8,834,666 B2 9/2014 Sreetharan et al.
2007/0206252 A1* 9/2007 Sissom .................. F16C 11/12
359/10
(Continued)

FOREIGN PATENT DOCUMENTS

WO 2012/109559 A1 8/2012
WO 2015/020952 A1 2/2015

OTHER PUBLICATIONS

J. Gafford, "Robust, Low-Cost and Modular mm-Scale Force Sensor", slide presentation at the 5th Annual Hamilton Symposium on Medical Robotics, London, UK (Jun. 22, 2015).
(Continued)

*Primary Examiner* — Michael P Stafira
(74) *Attorney, Agent, or Firm* — Modern Times Legal; Robert J. Sayre

(57) ABSTRACT

A light-intensity-based forced sensor comprises a Sarrus linkage, a biasing mechanism, a light emitter, and a light detector includes a first plate, a second plate, and at least one collapsible linkage pivotably coupled to both the first and the second plates. The biasing mechanism biases the collapsible linkage toward an extended configuration. The light emitter is coupled with and displaceable with the first plate; and the light detector is coupled with and displaceable with the second plate and configured to receive light emitted from the light emitter and generate an electrical signal in response to light received from the light emitter, wherein the generated electrical signal provides an indication of the distance between the first plate and the second plate. The sensor can be distally mounted on, e.g., an endoscope to provide haptic feedback at the distal end of the endoscope.

18 Claims, 9 Drawing Sheets

(51) Int. Cl.
G01L 1/24 (2006.01)
G01L 5/00 (2006.01)
A61B 1/06 (2006.01)
A61B 1/005 (2006.01)

(52) U.S. Cl.
CPC .............. *G01B 11/16* (2013.01); *G01L 1/248* (2013.01); *G01L 5/0038* (2013.01)

(56) References Cited

U.S. PATENT DOCUMENTS

| | | | | |
|---|---|---|---|---|
| 2013/0303847 | A1* | 11/2013 | Sitti | A61B 1/00158 600/104 |
| 2014/0202628 | A1* | 7/2014 | Sreetharan | H01L 41/25 156/257 |
| 2015/0366113 | A1* | 12/2015 | Sreetharan | E05D 1/00 16/225 |
| 2016/0184041 | A1* | 6/2016 | Gafford | B81C 99/0095 606/45 |
| 2017/0360279 | A1* | 12/2017 | Gafford | A61B 1/00096 |

OTHER PUBLICATIONS

J. Gafford, et al., "Robust, low-cost, modular mm-scale distal force sensors for flexible robotic platforms", Gafford J, Wood RJ, Walsh CJ. Robust, low-cost, modular mm-scale distal force sensors for flexible robotic platforms, in Proceedings of the 5th Annual Hamlyn Symposium on Medical Robotics, London, UK (Jun. 22, 2015).

J. Gafford, et al., "Self-Assembling, Low-Cost, and Modular mm-Scale Force Sensor", 16 IEEE Sensors Journal 69-76 (Jan. 1, 2016).

J. Gafford, et al., "A monolithic approach to fabricating low-cost, millimeter-scale multi-axis force sensors for minimally-invasive surgery", 2014 IEEE International Conference on Robotics and Automation 1419-1425 (May 31, 2014).

J. Gafford, et al., "Microsurgical Devices by Pop-Up Book MEMS", ASME/IDETC: Robotics and Mechanisms in Medicine, Portland, Oregon (Aug. 4, 2013).

* cited by examiner

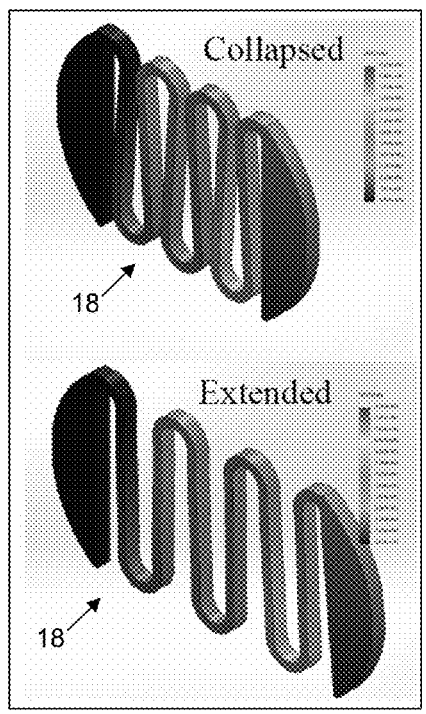
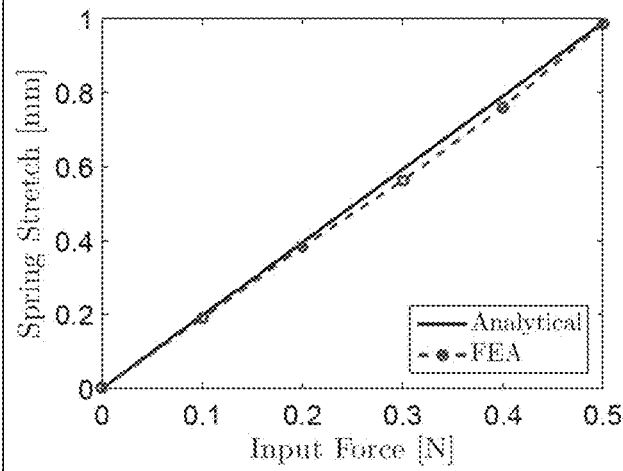
FIG. 8
FIG. 7
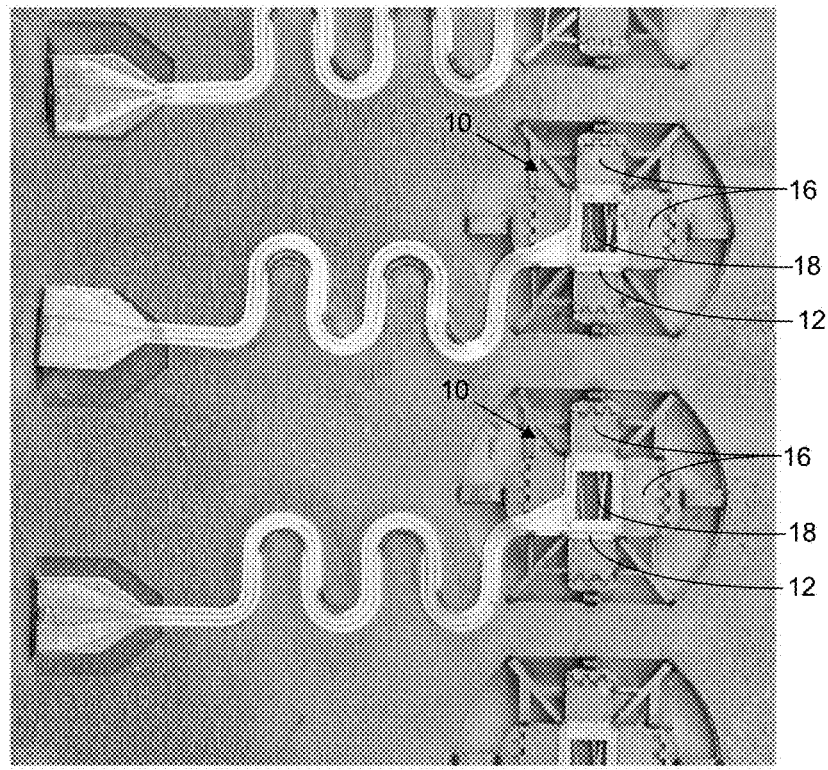
FIG. 9

MODULAR, MILLIMETER-SCALE, LIGHT-INTENSITY-BASED FORCE SENSING SYSTEM

BACKGROUND

Innovation in surgical robotics has seen a marked paradigm shift from rigid teleoperative systems towards flexible, cooperative and task-specific implementations. While substantial work has gone into the design and control of such systems, significant challenges arise in developing novel end-effector solutions at the scales required, which ultimately limits the sophistication and widespread applicability of these systems. These challenges arise from a general dependence on conventional meso- or micro-scale manufacturing approaches, which are not optimized to develop fully integrated assemblies at mm-scales in a cost-effective manner. Furthermore, developing robust distal sensing modalities that can be easily integrated into mm-scale packages proves to be a significant challenge from a manufacturing and assembly perspective.

Several groups have recognized this challenge and are developing unique solutions to enable distal force sensing for flexible surgical procedures; and a lot of interest has been generated, both academically and commercially, in recent years in using fiber-based optical force sensing methods (such as fiber Bragg gratings, Fabry-Perot interferometry, and light-intensity modulation) for force feedback in catheters and flexible surgical robots and shape estimation of flexible tooling. In 2014, the ThermoCool SmartTouch ablation catheter (BioSense Webster), which employs light intensity modulation to resolve distal forces in 3 axes, achieved FDA-approval to become the first commercially available ablation catheter to feature fiber-based force feedback in real-time. Such a development is a pivotal step towards widespread acceptance and adoption of force sensing methodologies in minimally invasive procedures. While offering unprecedented resolution (<mN) in a compact package, the entire device is designed around optical transmission fibers that occupy valuable space that can otherwise used for working ports or lumens. In addition, expensive interrogators and signal-conditioning equipment are often necessary to convert the signal into a meaningful quantity that can be post-processed. Furthermore, optical fibers are sensitive to deformation for which compensation must be provided (usually with a biasing fiber) to generate a pure reading of the distal force.

SUMMARY

A light-intensity-based force sensor for distal inclusion in a catheter/endoscope system and methods for its use and fabrication are described herein, where various embodiments of the apparatus and methods may include some or all of the elements, features and steps described below.

The light-intensity-based forced sensor comprises a Sarrus linkage, a biasing mechanism, a light emitter, and a light detector includes a first plate, a second plate, and at least one collapsible linkage pivotably coupled to both the first plate and the second plate, wherein the collapsible linkage is configured to change a distance between the first plate and the second plate as the collapsible linkage collapses or extends along a longitudinal axis. The biasing mechanism is coupled with the collapsible linkage to bias the collapsible linkage toward an extended configuration, wherein the first plate and the second plate are separated by a maximum distance. The light emitter is coupled with and displaceable with the first plate; and the light detector is coupled with and displaceable with the second plate and configured to receive light emitted from the light emitter and generate an electrical signal in response to light received from the light emitter, wherein the generated electrical signal provides an indication of the distance between the first plate and the second plate.

The Sarrus linkage, with the collapsible linkage in a collapsed state, can have a height and width (dimensions orthogonal to the longitudinal axis of the endoscope working channel) that are each no greater than 3 mm, wherein the height and width are orthogonal to the longitudinal axis along which the collapsible linkage extends and collapses. The first plate, the collapsible linkage, and the biasing mechanism can be configured to place the first plate at decreasing distance from the second plate as a force toward the second plate is placed upon the first plate. The light emitter and the light detector can also be configured so that the light detector generates the electrical signal with an increasing intensity as the distance between the first plate and the second plate decreases.

The distally incorporated light-intensity-based forced sensor can include a plurality of the collapsible linkages; and each of the collapsible linkages can include an intermediate hinge midway along its length. The biasing mechanism can also include a spring coupled with opposing collapsible linkages.

In particular embodiments, the light emitter is an infrared light-emitting diode, and the light detector is an infrared phototransistor. Further still, flex-circuits can be coupled with the light emitter and with the light detector.

In additional embodiments, the first plate, the second plate, and the collapsible hinge, each comprise a rigid segment and a flexible layer extending from the rigid segment, wherein the flexible layer has a flexural modulus at least 5 times greater than the rigid segments; and wherein the collapsible hinge is coupled with the first and second plates via the flexible layer at gaps between the rigid segments.

The light-intensity-based force sensor can be mounted at a distal end of an endoscope or other catheter. In particular embodiments, the distally mounted sensor can further include a computer processor in communication with the light detector and computer-readable memory in communication with the computer process and non-transiently storing software code for correlating light-intensity measurements from the light detector with force exerted on the first plate as well as a power source coupled with the light emitter. All of these electronic components can, therefore be distally mounted on the tool.

In a method for distal light-intensity-based force sensing, an elongated tool with a sensor mounted on its distal end is inserted, distal end first, into a passageway. The light emitter then emits light directed toward the light detector, and the light incidence on the light detector is measured. When at least one surface in the passageway is contacted with the first plate and when that contact exerts a force on the first plate that displaces the first plate toward the second plate, the incidence of the light from the light emitter upon the light detector increases. A measurement of increased light incidence measured by the light detector is then correlated with the force exerted on the first plate.

The passageway can be in a human body, and the elongated tool can be an endoscope. The sensor can be at a distal end of a catheter passing through a channel defined in the endoscope. In one example, the endoscope is used to perform an electrograde cholangeopancreatography.

The sensor components can be formed of biocompatible materials, such as stainless steel, titanium, Kapton polyamide, etc., to avoid triggering an autoimmune response when inserted in the human body.

The light-intensity-based force sensor can be self-assembling and can be manufactured using a composite lamination fabrication process, wherein linkages pre-machined in the laminate provide the required degrees-of-freedom and fold patterns to facilitate self-assembly. Using purely two-dimensional fabrication techniques, energy contained within a planar elastic biasing element directly integrated into the laminate is released post-fabrication, allowing the sensor to 'self-assemble' into its final three-dimensional shape. The sensors can be batch-fabricated, further driving down production costs. The transduction mechanism relies on the principle of light intensity modulation, which allows the sensor to detect axial forces with mN-level resolution. The geometry of the sensor was selected based on size constraints inherent in minimally-invasive surgery, as well as with specific focus on optimizing the sensor's linearity. The sensor is unique from fiber-based force sensors in that the emitter and the detector are encapsulated within the sensor itself. The bare sensor can operate over a force range of 0-200 mN, with a sensitivity of 5 V/N and a resolution of 0.8 mN. Experimental results show that the sensor's stiffness can be tuned by (a) using a thicker material for the spring layer and/or (b) encapsulation/integration with soft materials. Empirical validation shows that the sensor has the sensitivity and resolution necessary to discern biologically relevant forces in a simulated cannulation task.

With increasing clinical interest in force-sensing capabilities on-board very small (e.g., <3 mm outer-diameter) packages, the apparatus and methods described herein can offer an advantageous innovation in this field, particularly in terms of improving sensitivity and modularity while reducing cost. Additionally, the use of optical (light-based) sensing allows for measurement of a broader range of forces, wherein the measurements are no particularly subjected to conditions that may cause interference (e.g., changes in temperature that change the electrical response of a strain gauge). Moreover, the use of infrared light insulates the light detector readings from the potential interference of ambient (visible) light on the detector.

In particular embodiments, the sensor can be distally mounted on an endoscope to perform endoscopic retrograde cholangio-pancreatography or endoscopic submucosal dissection, thoracic procedures (e.g., surgery in the lungs), and for surgical procedures in the prostate or in the reproductive tubes of a human. In this context, the sensor can provide distal haptic (tactile) feedback to the operator of the endoscope. The endoscope can have an outer diameter, e.g., of 8 mm and can define a working channel with a diameter between 2.7 and 3.2 mm; and the sensor can have dimensions orthogonal to the longitudinal (longest) dimension of the straightened endoscope that are less than the diameter of the working channel. For example, the sensor can have dimensions no greater than 2.7 mm.

BRIEF DESCRIPTION OF THE DRAWINGS

FIG. 7 illustrates representative displacement of a spring 18 (collapsed at top and extended at bottom) during finite element analysis (FEA) trials.

FIG. 8 plots a comparison between FEA results (circles and dashed line) and the numerical model (solid line) given in Equation 12.

FIG. 9 is a photographic image of batch-fabricated sensors 10 prior to release and self-assembly.

Figure 1:
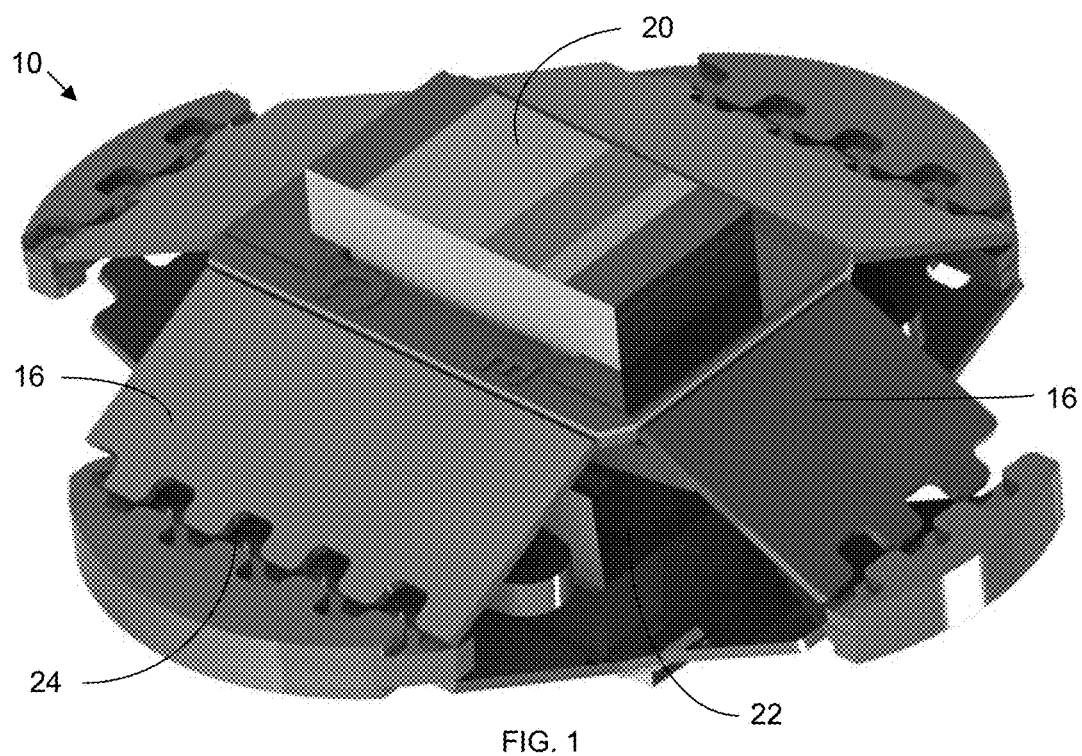
FIGS. 1 and 2 provide a conceptual rendering of self-assembling force sensor 10.

In the accompanying drawings, like reference characters refer to the same or similar parts throughout the different views; and apostrophes are used to differentiate multiple instances of the same or similar items sharing the same reference numeral. The drawings are not necessarily to scale; instead, an emphasis is placed upon illustrating particular principles in the exemplifications discussed below.

DETAILED DESCRIPTION

The foregoing and other features and advantages of various aspects of the invention(s) will be apparent from the following, more-particular description of various concepts and specific embodiments within the broader bounds of the invention(s). Various aspects of the subject matter introduced above and discussed in greater detail below may be implemented in any of numerous ways, as the subject matter is not limited to any particular manner of implementation. Examples of specific implementations and applications are provided primarily for illustrative purposes.

Unless otherwise herein defined, used or characterized, terms that are used herein (including technical and scientific terms) are to be interpreted as having a meaning that is consistent with their accepted meaning in the context of the relevant art and are not to be interpreted in an idealized or overly formal sense unless expressly so defined herein. For example, if a particular composition is referenced, the composition may be substantially (though not perfectly) pure, as practical and imperfect realities may apply; e.g., the potential presence of at least trace impurities (e.g., at less than 1 or 2%) can be understood as being within the scope of the description. Likewise, if a particular shape is referenced, the shape is intended to include imperfect variations from ideal shapes, e.g., due to manufacturing tolerances. Percentages or concentrations expressed herein can be in terms of weight or volume. Processes, procedures and phenomena described below can occur at ambient pressure (e.g., about 50-120 kPa—for example, about 90-110 kPa) and temperature (e.g., −20 to 50° C.—for example, about 10-35° C.) unless otherwise specified.

Although the terms, first, second, third, etc., may be used herein to describe various elements, these elements are not to be limited by these terms. These terms are simply used to distinguish one element from another. Thus, a first element, discussed below, could be termed a second element without departing from the teachings of the exemplary embodiments.

Spatially relative terms, such as "above," "below," "left," "right," "in front," "behind," and the like, may be used herein for ease of description to describe the relationship of one element to another element, as illustrated in the figures. It will be understood that the spatially relative terms, as well as the illustrated configurations, are intended to encompass different orientations of the apparatus in use or operation in addition to the orientations described herein and depicted in the figures. For example, if the apparatus in the figures is turned over, elements described as "below" or "beneath" other elements or features would then be oriented "above" the other elements or features. Thus, the exemplary term, "above," may encompass both an orientation of above and below. The apparatus may be otherwise oriented (e.g., rotated 90 degrees or at other orientations) and the spatially relative descriptors used herein interpreted accordingly.

Further still, in this disclosure, when an element is referred to as being "on," "connected to," "coupled to," "in contact with," etc., another element, it may be directly on, connected to, coupled to, or in contact with the other element or intervening elements may be present unless otherwise specified.

The terminology used herein is for the purpose of describing particular embodiments and is not intended to be limiting of exemplary embodiments. As used herein, singular forms, such as "a" and "an," are intended to include the plural forms as well, unless the context indicates otherwise. Additionally, the terms, "includes," "including," "comprises" and "comprising," specify the presence of the stated elements or steps but do not preclude the presence or addition of one or more other elements or steps.

Additionally, the various components identified herein can be provided in an assembled and finished form; or some or all of the components can be packaged together and marketed as a kit with instructions (e.g., in written, video or audio form) for assembly and/or modification by a customer to produce a finished product.

Figure 2:
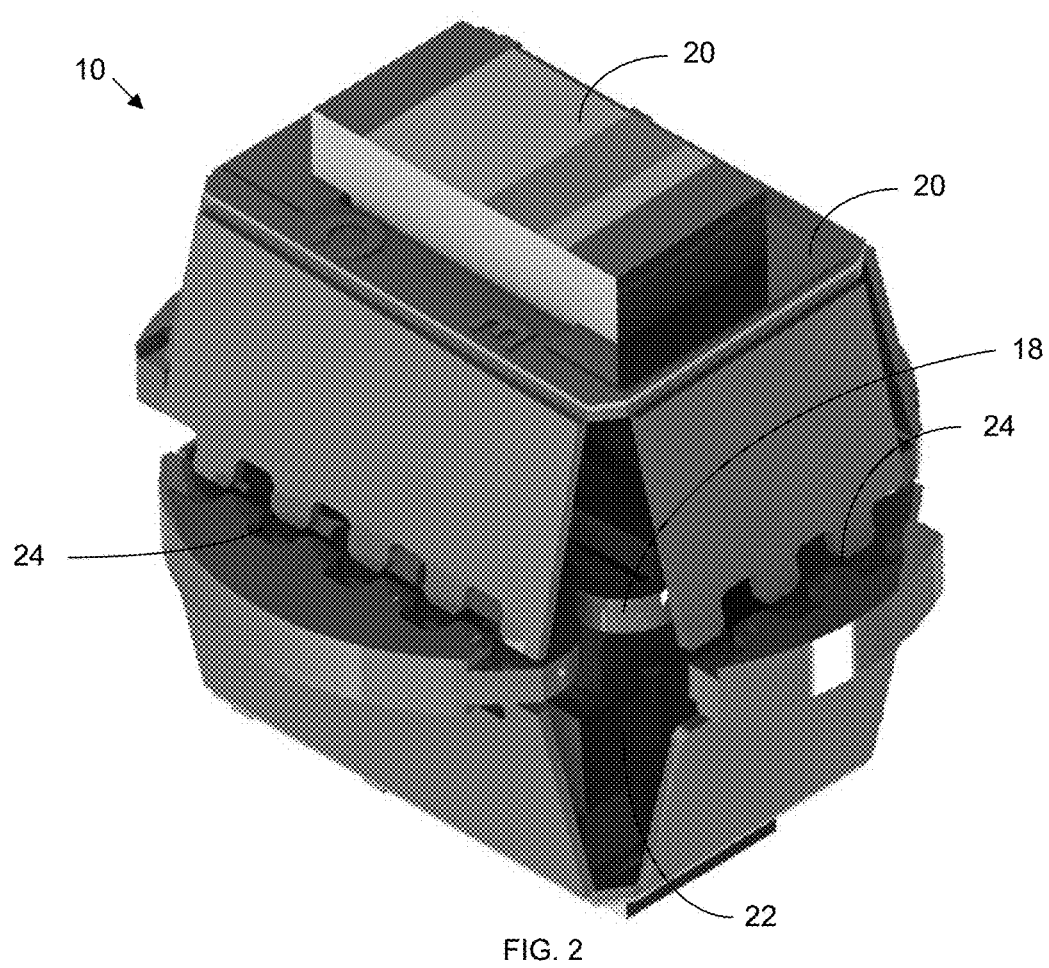

Introduction:

Prior work [see J. Gafford, et al., "Monolithic Fabrication of Millimeter-Scale Multi-Axis Force Sensors for Minimally Invasive Surgery", IEEE International Conference on Robotics and Automation (2014), and J. Gafford, et al., "Microsurgical Devices by Pop-Up Book MEMS", ASME/IDETC: Robotics and Mechanisms in Medicine (2013)] has demonstrated the ability to integrate sensors and mechanisms using a monolithic laminate manufacturing process. This prior work is herein built upon to develop a novel, fully distal, light-intensity-based force sensor 10 (see FIGS. 1 and 2) that removes the need for optical fiber transmission from a proximal source. With the emitter 20 and detector 22 contained fully incorporated into the distally integrated sensor 10, legacy devices can be outfitted with this force sensor 10 to provide force-sensing capabilities without having to re-design the entire delivery system around the inclusion of optical fibers that must run along the entire length of the device. The absence of fiber transmission results in an extremely stable signal that is not affected by the shape of the delivery system. The ultra-small footprint (2.7 mm) of the force sensor 10 means such a sensor 10 can pass through the working port of an 8.6-mm-diameter endoscope, opening up the possibility of "sensorizing" electrosurgical tools for intraluminal interventions.

The discussion, below, begins with a discussion on the theory of sensor 10 operation and presents a mechanical model used to design and optimize the design of the sensor 10 for linear operation. The sensor 10 is then calibrated and validated in a benchtop environment. To demonstrate the capability of modular integration, the sensor 10 is molded into a mock-up catheter, and force data is recorded in a simulated cannulation task.

Figure 3:
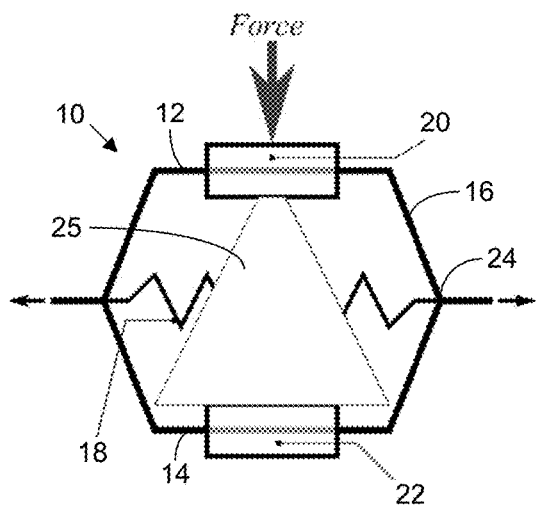
FIG. 3 is a simplified schematic of a sensor 10 in operation.

Theory of Operation:

The sensor 10 operates by the principle of light-intensity modulation. As illustrated in the simplified schematics of FIGS. 3 and 4, four orthogonal Sarrus linkage segments 16 (each with an intermediate hinge 24) couple a first (top) plate 12 and a second (bottom) plate 14, to which an emitter 20 and a detector 22 are connected (respectively). By varying the distance, h, separating the source from the detector 22 by a displacement, $\delta_h$, the amount of light 25 (energy) reaching the detector 22 is modulated. Depending on the sensing modality of the collector, a measurable electrical quantity (drain current, voltage) generated by the detector 22 is directly proportional to the detected energy of the incident light 25. Through proper calibration, the change in this quantity can be related to the applied force.

The force sensor 10, described herein, can include a monolithically fabricated hexagonal prism. An energy source, e.g., an infrared light emitting diode (e.g., IR LED) 20, is attached to the top face, and a light detector (e.g., IR phototransistor 22) is attached to the bottom face. As a force is applied to the top face, the box is 'collapsed', thereby bringing the source closer to the detector 22. This displacement directly correlates to a change in intensity measured by the detector 22, which can be related to the applied force. As the box collapses, an integrated spring 18 provides a reaction force that ultimately determines the "sensitivity" of the sensor 10 and restores the sensor 10 configuration to its un-collapsed state when the force is removed. Orthogonal Sarrus linkage segments 16 constrain motion to the longitudinal sensing axis (oriented vertically in FIGS. 3 and 4).

The sensor 10 can also include a computer processor (also mounted on or in the distal laminate structure), wherein the computer processor is in communication with (e.g., via electrically conductive wiring) the light detector 22 and with a computer-readable storage medium (memory), which can be mounted alongside the computer processor at the distal end of the tool. The computer memory stores software code for correlating the light-intensity measurements from the light detector 22 with a force exerted on the first end plate 12; and the correlated force can be communicated to the operator of the tool (e.g., a surgeon). The light-intensity-based force sensor 10 can also include power source (e.g., a battery), such that all electronic components can be mounted in/on the sensor 10 at the distal end of the elongated tool.

Figure 4:
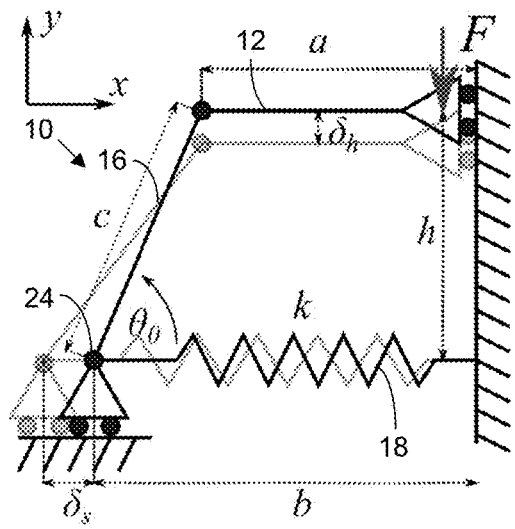
FIG. 4 is a simplified mechanical schematic used in the derivation of the sensor's kinematics.

Mechanical Model:

Considering once again the schematic shown in FIG. 4, one can determine how much the spacing, h, changes given a known input force, F, which in turn, allows determination of the irradiance, $E_{PT}$, reaching the phototransistor 22 based on a simple point source model assuming certain assumptions are satisfied. From the geometry of the structure, only the x component of the applied force goes into stretching the bias spring 18, according the following equation:

$$F \cos(\theta) = k_s \delta_s, \qquad (1)$$

where $\theta$ is the hinge angle, $k_s$ is the spring coefficient, and $\delta_s$ is the amount of spring 18 deformation. From a purely geometric argument, $\theta$ can be related to other geometric parameters that describe the sensor 10, as well as the spring 18 stretch, $\delta_s$, as follows:

$$\theta = \arccos\left(\frac{b + \delta_s - a}{c}\right). \qquad (2)$$

Equating Equations 1 and 2 produces the following:

$$\arccos\left(\frac{k_s \delta_s}{F}\right) = \arccos\left(\frac{b + \delta_s - a}{c}\right), \qquad (3)$$

where a, b and c are geometric variables. Taking the cosine of each side and re-structuring leaves an analytical expression for the spring 18 stretch, $\delta_s$, given an input force, F, as follows:

$$\delta_s = \frac{F(b-a)}{ck_s - F}. \qquad (4)$$

A geometric argument also provides the following:

$$h - \delta_h = c \sin(\theta), \qquad (5)$$

where $$h = \sqrt{c^2 - (b-a)^2}. \qquad (6)$$

Plugging Equation 4 into Equation 2 produces the following analytical expression relating input force, F, to displacement, $\delta_h$:

$$\delta_h = \sqrt{c^2 - (b-a)^2} - c \sin\left(\arccos\left(\frac{b + \frac{F(b-a)}{ck_s - F} - a}{c}\right)\right). \qquad (7)$$

Optoelectronic Model:

As $\delta_h$ is not a directly observable quantity, the mechanical model is expanded upon to generate an expression for the collector current drained by the phototransistor 22 as a function of the force applied to the sensor 10. For this endeavor, a very simple model is considered, treating the light emitting diode (LED) 20 as a point source that emits a radiant intensity, $I_{LED}$, that is spread out uniformly over the surface area of a hemisphere, which is a suitable approximation provided the spacing between the emitter 20 and the detector 22 satisfies the "far-field" condition. The irradiance, $E_{PT}$, that strikes the phototransistor 22 is given by the following (simplified) expression:

$$E_{PT} = \frac{I_{LED}}{(h - \delta_h)^2}. \qquad (8)$$

The quantity, $I_{LED}$, is logarithmically related to the LED 20 forward current, $i_{LED}$, as follows:

$$I_{LED} = \exp(\alpha_1 \log(i_{LED}) + \beta_1), \qquad (9)$$

where $\alpha_1$ and $\beta_1$ are specified by manufacturer data sheets.

Assuming the forward current through the LED 20 is fixed, $I_{LED}$ is constant, and henceforth, treated as such.

Figure 5:
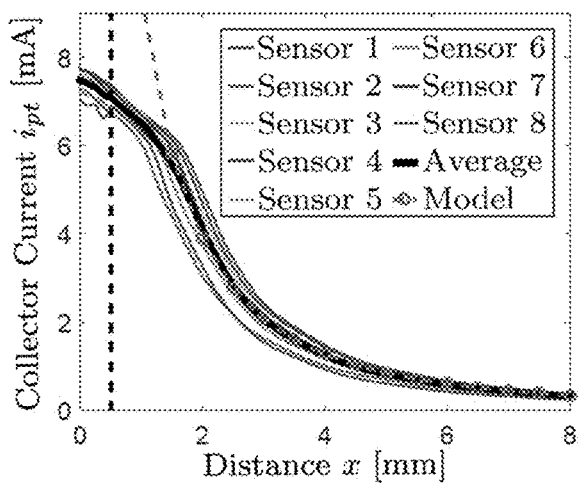
FIG. 5 plots the collector current, $i_{PT}$, from the detector 22 as a function of distance from the light emitting diode (LED) source.

The collector current, $i_{PT}$, as a function of incident irradiance, $E_{PT}$, is similarly exponentially related, as follows:

$$i_{PR} = \exp(\alpha_2 E_{PT} + \beta_2), \qquad (10)$$

where $\alpha_1$ and $\beta_2$ are specified by manufacturer data sheets. The digitized transfer functions illustrating Equations 9 and 10 are shown in FIG. 5. Putting everything together, the final expression is:

$$i_{PT} = \exp\left(\alpha_2 \log\left(\frac{I_{LED}}{(h - \delta_h)^2}\right) + \beta_2\right), \qquad (11)$$

where $\delta_h$ is as defined in Equation 7.

Verification:

To experimentally validate the optoelectronic model, a precision positioning system was fabricated to enable the characterization of the phototransistor 22 response as a function of distance from the LED 20. The system features an encoded DC motor with a 100:1 planetary gearhead that transmits motion to a linear carriage attached to a ¼-20 leadscrew via a worm gear drive that offers an additional 24:1 speed reduction. A 500 counts-per-revolution (CPR) optical encoder is mounted to the worm shaft, giving the system a theoretical positioning resolution of 800 nm barring any backlash within the leadnut. An analog slide potentiometer is attached to the linear carriage for absolute encoding. 10-bit data were captured at a rate of 100 Hz via an Arduino MEGA 2560 microcontroller board.

An array of eight stationary IR LEDs 20 were aligned with a similar array of phototransistors 22 mounted on the moving carriage. The phototransistor array was moved from absolute minimum distance (saturation) to a distance of 9 mm away from the LED array 20 at a constant speed of 125

µm/s. The LEDs 20 and phototransistors 22 were independently addressed to eliminate cross-talk.

Figure 6:
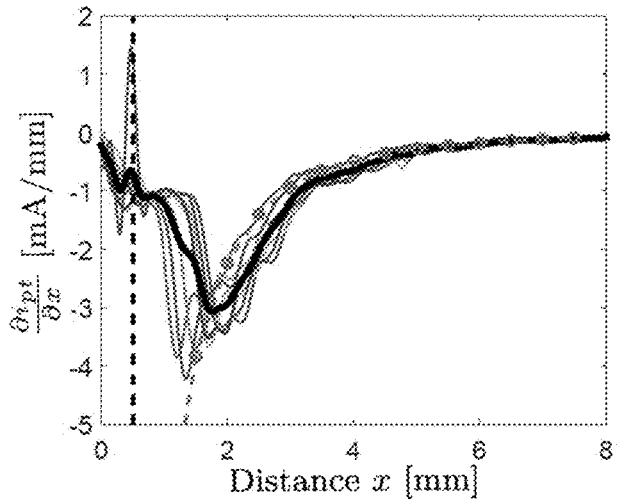
FIG. 6 plots the sensor's sensitivity, $\delta_{iPT}/\delta_x$. The dotted line shows the theoretical far-field cutoff given by the Lambertian simplification.

Results of this study are shown in FIGS. 5 and 6. Typical far-field behavior is observed and is accurately modeled by a decaying exponential. These plots also show how the experimental data very accurately match the optoelectronic model over the far-field regime but deviate from the model near the Lambertian cutoff, when the point-source (far-field) simplification is no longer a valid assumption. Note that typical near-field behavior is characterized by a sharp drop to zero output as the separation distance approaches zero. The LED 20 and phototransistor 22 in this embodiment, however, are hard-molded in 500-µm-thick resin that provides an inherent distance offset of 1 mm between the emitter 20 and detector 22; and as such, the emitter 20 and detector 22 cannot be positioned close enough to exploit this near-field behavior. FIG. 6 also shows a peak (roughly constant) sensitivity at between 1.5 and 2 mm separation distance between the light emitter 20 and detector 22. In particular embodiments, this "sweetspot" is exploited in an attempt to linearize the behavior while optimizing the sensitivity.

Other Linearity Considerations:

As is evident in Equation 11, the predicted behavior is highly nonlinear and can lead to special design considerations, such that the sensor 10 only operates in the linear regime. The nonlinearities arise from (1) the geometry of the sensor 10, in which the actual force transmitted to the spring 18, as shown in FIG. 7, is a function of the cosine of the hinge angle, (2) the exponential dependence of the collector current on the incident irradiance, and (3) the inverse square relationship between irradiance and distance. In order to further guide the design with the added constraint of sufficient linearity, an algorithm was implemented in MATLAB to determine how some aspects of sensor design (namely, initial spacing, h, and spring thickness, $t_s$) affect the force range over which the behavior is "sufficiently linear" (or, in this case, when the residual of a best-fit line to the curve of $i_{PT}$ versus F is 0.90 or greater). Note that, for simplicity of analysis, the spring stiffness, $k_s$, is modeled as follows:

$$k_s = \frac{3EI}{NL^3}, \quad (12)$$

where E is the Young's Modulus of the material (200 GPa for 304 Stainless Steel);

$$I = \frac{wt_g^3}{12}$$

is the second moment of area of each beam in the serpentine pattern; N is the number of "switchbacks" in the pattern; and L is the length of each beam in the pattern. To validate this simplification, the model was compared to finite element analysis (FEA) displacement results performed on a spring 18 with a thickness of 0.006 inch. The results shown in FIG. 8 demonstrate that the linear simplification is a very good approximation of the behavior.

Increasing the spring 18 thickness (and, therefore, the stiffness) results in the most dramatic increase in linear force range, while reducing the resolution. Additionally, the sensitivity, $$S = \frac{\delta i_{PT}}{\delta F}$$

(here, it is simply the slope of the best-fit line) drops off substantially by increasing the stiffness and the spacing. Thus there is a significant tradeoff between linearity range and sensitivity. Given size constraints and material constraints, an initial sensor 10 spacing of 1 mm was selected along with a spring 18 thickness of 100 µm. Note that this spacing is also chosen to satisfy the far-field condition of the LED source 20 (h/D>5, where D is the Lambertian source size of the LED). These parameters provide an expectation of decent linearity over 120 mN of applied force.

Fabrication:

With the geometry of the sensor 10 determined, the sensor 10 was fabricated using a composite laminate fabrication process herein referred to as pop-up MEMS or PCMEMS (see U.S. Pat. No. 8,834,666 B2 and PCT Application Pub. No. WO 2015/020952 A1 for a description of the fabrication process). Four layers of 304 stainless steel comprise the mechanical structure of the sensor 10. DuPont FR1500 acrylic adhesive joins layers together. Copper-clad Kapton polyimide (from E. I. du Pont de Nemours and Company) is laminated on the top and bottom surfaces to provide electrical contacts for the LED 20 and phototransistor 22, as well as flex-circuit breakouts for wiring to peripheral architectures.

Initial Processing:

Individual material layers are machined using a diode-pumped solid-state (DPSS) laser. Traces are manufactured on the copper-clad Kapton polyimide layers using a direct-write photolithography process. The surfaces of each layer are treated using an argon plasma etching process to promote adhesion, and the layers are placed into an alignment jig laminated together using heat and pressure. Prior to the lamination process, the spring layer 18 is pre-stretched from a collapsed (FIG. 7, top) to an extended (FIG. 7, bottom) configuration when placed into the alignment jig. The curing process serves to lock the spring 18 into a stretched configuration via adhesion to adjacent layers. FIG. 9 shows what the sensor batch looks like just after the lamination process, prior to release. Sacrificial ribs suspend the sensor body within the alignment scaffold, allowing for easy removal after release cuts are made. The pre-stretched spring 18 can be seen through the "window" into which the LED 20 will be pressed.

Release and Self-Assembly:

Release cuts are performed in the DPSS laser to sever the sensor's connection to the alignment scaffold. Once release cuts are made (e.g, via a laser cut 34), the spring 18 is no longer constrained and is free to retract under its own elasticity; however, a kinematic singularity prevents the spring 18 from retracting and assembling the mechanism in the flat state (the spring 18 restoring force is in line with the neutral axes of the flexural joints). To overcome this singularity, released sensors 10 are submerged in an ultrasonic bath of isopropyl alcohol, which provides the agitation required (and has the added benefit of ridding the sensor 10 of any debris/residue left over by the release cut operation). Once the spring 18 is able to snap past this singularity, it retracts and assembles the sensor 10 into its 3-dimensional shape. Cutouts and fiducials in the laminate allow for the LED 20 and phototransistor 22 to be press-fit into place, where they are reflow soldered to the sensor contact pads.

Figure 10:
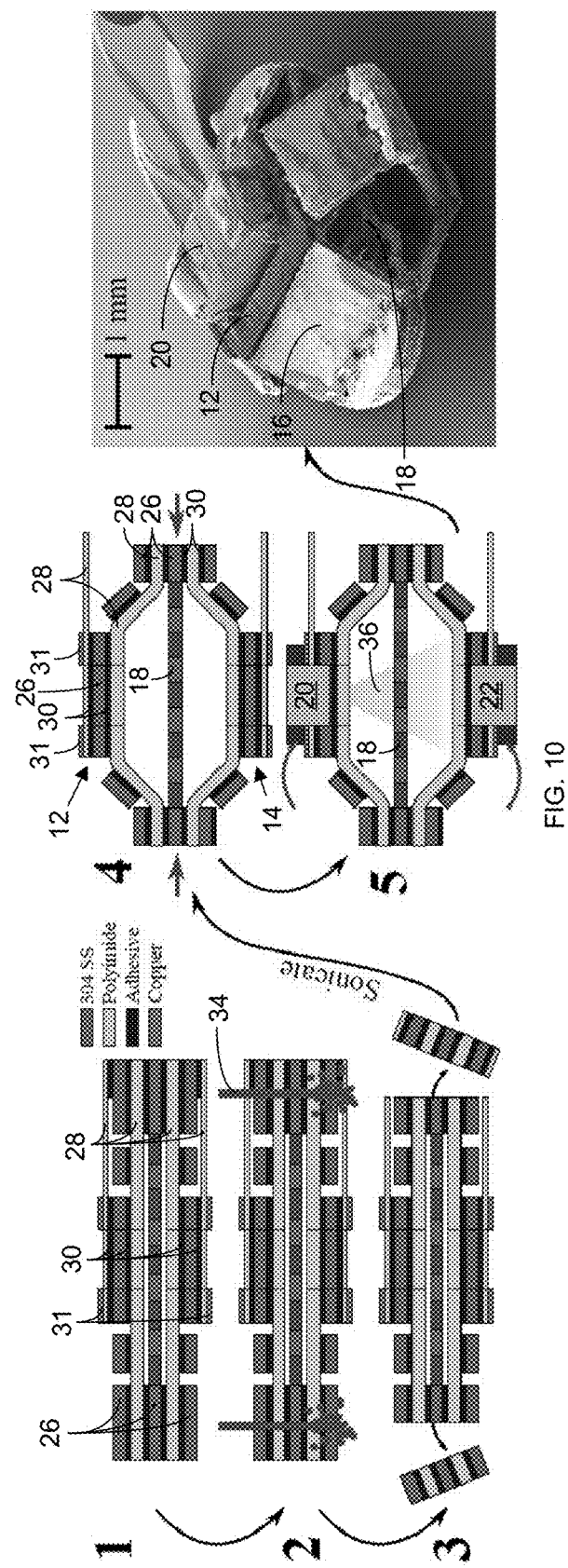
FIG. 10 shows a sequence of steps in the release and self-assembly of a sensor 10. Step 1 shows a laminate framework for a sensor 10 after curing of the laminate. Step 2 shows release cuts made with a DPSS laser to release the structure and remove the constraints on the spring 18. Step 3 shows discarding of the alignment scaffold after the release cuts are made. Step 4 shows the structure when submerged in an ultrasonic bath, wherein the agitation causes the spring 18 to overcome the kinematic singularity, thereby retracting and assembling the structure. Step 5 shows the pick-and-place insertion of a light emitting diode (LED) 20 and phototransistor (PT) 22 into the structure to form the sensor 10. Finally, the photographic image provides a magnified view of a sensor 10 following step 5.

Integrated flex circuitry allows for straightforward wiring to a data acquisition unit. This process is illustrated in FIG. 10, which shows the laminate structure comprising a laminated stack of the following layers (from top to bottom): conductor (copper) 31, flexible layer (polyimide) 28, adhesive layer 30, rigid segments (stainless steel) 26, adhesive layer 30, flexible layer (polyimide) 28, adhesive layer 30, rigid segments (stainless steel—including spring 18) 26, adhesive layer 30, flexible layer (polyimide) 28, adhesive layer 30, rigid segments (stainless steel) 26, adhesive layer 30, flexible layer (polyimide) 28, adhesive layer 30, and conductor (copper) 31. the light emitter (LED) 20, which emits an outwardly expanding beam of infrared light 36.

Figure 11:
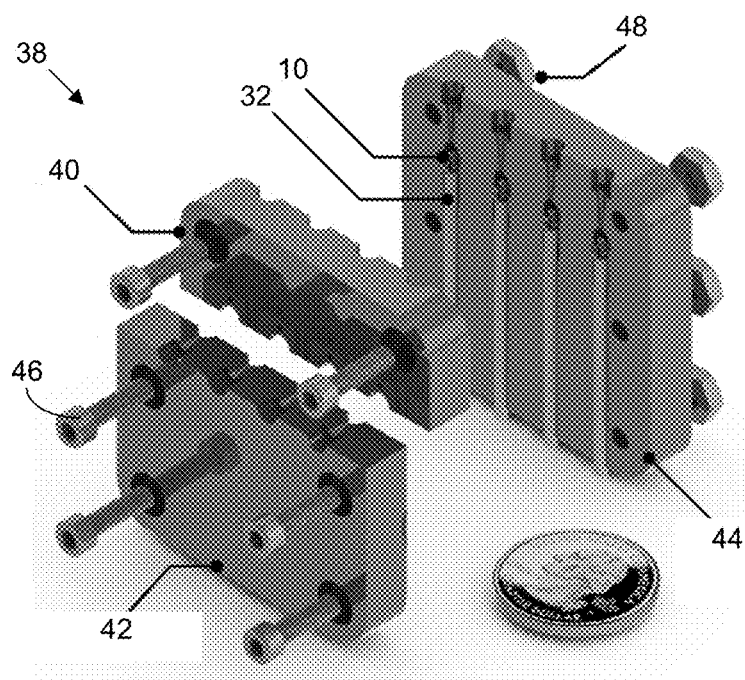
FIGS. 11 and 12 illustrate the details of a mold for encapsulation and integration of a sensor 10 onto a 2 mm-diameter (6F) catheter 32 with a US quarter providing a sense of scale in FIG. 11.
Figure 12:
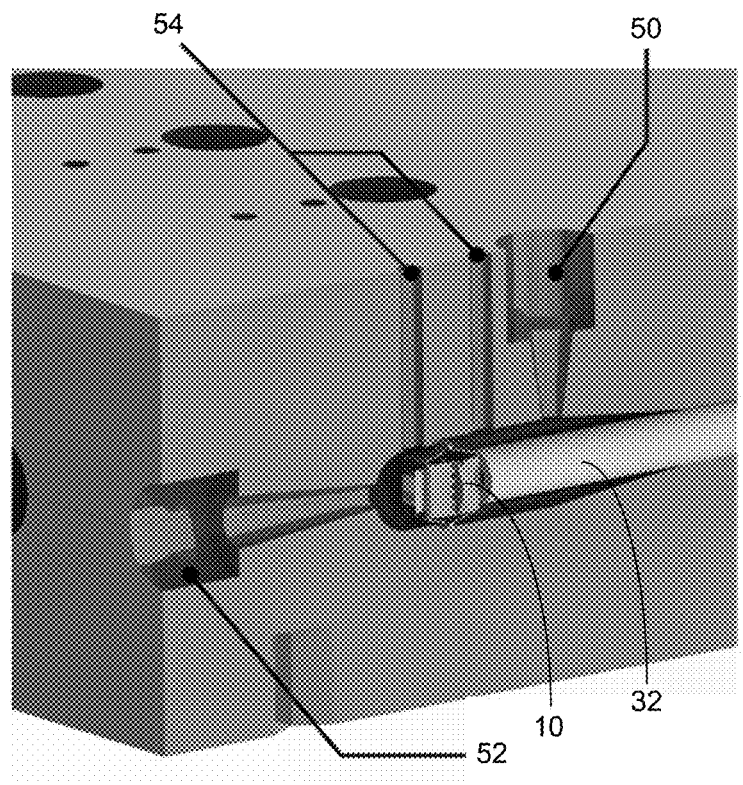
Figure 13:
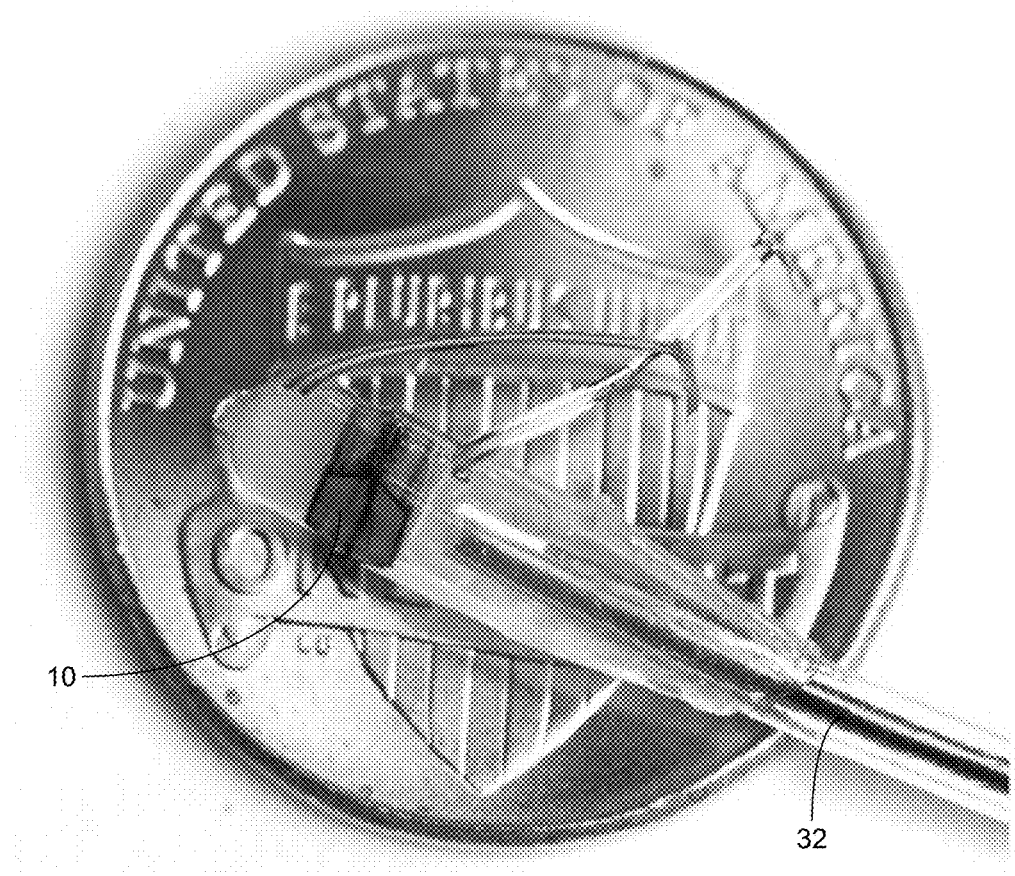
FIG. 13 is a photographic image showing encapsulation and integration of a sensor 10 onto a 2-mm (6F) catheter 32 with a US penny backdrop providing a sense of scale.

Molding and Integration:

The sensor 10 was integrated into a dummy catheter 32 by means of a molding process. The mold 38 includes two top mold sections 40 and 42 and a bottom mold section 44 held together with screws 46 and captive nuts 48. Three-part mold 38 that contain alignment features for locating the sensor 10 and catheter tube in space were 3D-printed (see FIGS. 11 and 12). The sensor 10 was press-fitted into the mold 38, and a small bead of ultraviolet (UV)-cure epoxy was applied to temporarily fixate the sensor 10 to the catheter 32. Sensor electrical traces were routed outside of the mold 38. The mold 38 was filled using a top and lateral inflow sprues 50 and 52 and outflow risers 54 with a pre-degassed low-durometer silicone rubber (EcoFlex 00-50), which is transparent to infrared (IR) light. After sufficient curing time, the molded catheters are released from the mold 38. FIG. 13 shows the sensorized catheter after release.

Figure 14:
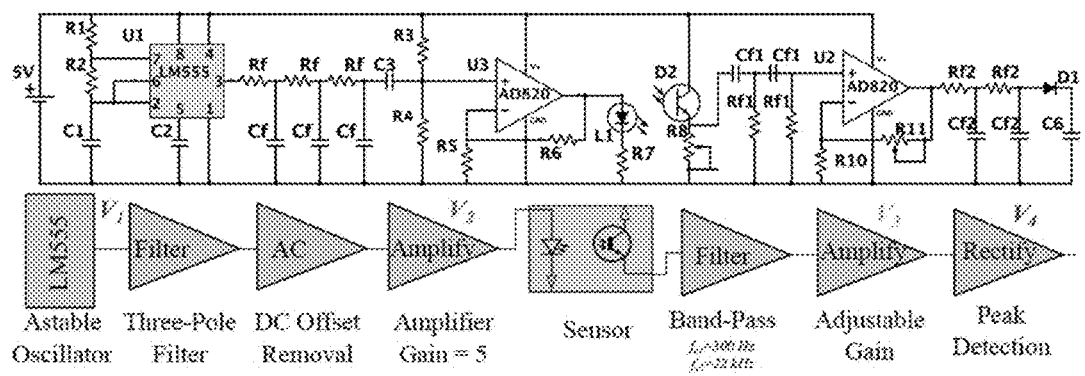
FIG. 14 is a schematic illustration of electrical architecture for the source excitation and filtering of the phototransistor response.
Figure 15:
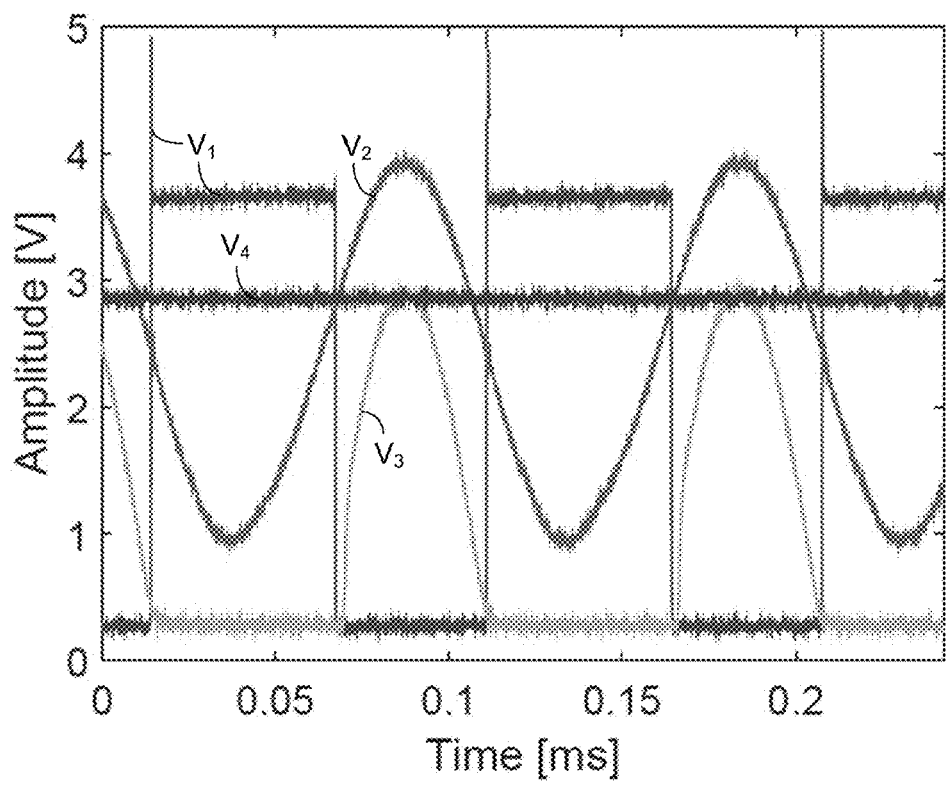
FIG. 15 plots representative scope traces at various locations along the conditioning circuitry.

Signal Conditioning:

Light-based sensing modalities are notoriously susceptible to ambient conditions. Although the IR phototransistor 22 has peak spectrum response to 940-nm-wavelength IR radiation, the spectral bandwidth ranges from 400-1100 nm; and, as such, the sensor 10 is sensitive to visible light. To overcome this sensitivity to interference, AC-coupling is introduced into the conditioning circuitry so that the system only responds to a very narrow band of input frequencies in the temporal domain to isolate the response, as shown in FIG. 14. An LM555 timer, configured as an astable oscillator, provides a square wave with a frequency of $f_{555}=7$ kHz. However, a square wave is not an ideal excitation source due to the high frequency content of the rising/falling edges, which are difficult to filter in subsequent stages. To remedy this difficulty, the square wave is passed through a three-pole RC filter that produces an approximation of a 8-kHz sine wave with reduced amplitude and an offset of $V_{offset}=0.5\ V_{cc}$. This wave is AC-coupled to remove the offset and passed through a non-inverting amplifier to produce a sine wave with 5 $V_{pp}$. This wave is used to drive the IR LED 20. The phototransistor 22 collector current is converted into a voltage by a variable resistor, $R_8$; and this voltage is sent through a double-pole band-pass filter with a center frequency at 8 kHz and a quality factor of Q=0:67 (resulting in a loss of −1.5 dB at 8 kHz). The high-pass and low-pass filter stages within the band-pass filter are buffered by an adjustable-gain non-inverting amplifier. A passive peak detector converts the AC-signal into a DC signal that can be processed by a data acquisition unit. Note that there is an additional low-pass filter inherent in the phototransistor 22 response (with a cutoff of roughly 23 kHz, estimated by $f_c=0.35/(\tau_r)$, where $\tau_r$ is the rise time of the phototransistor 22 (15 μS). Representative scope traces at various locations along the conditioning circuitry are plotted in FIG. 15.

Figure 16:
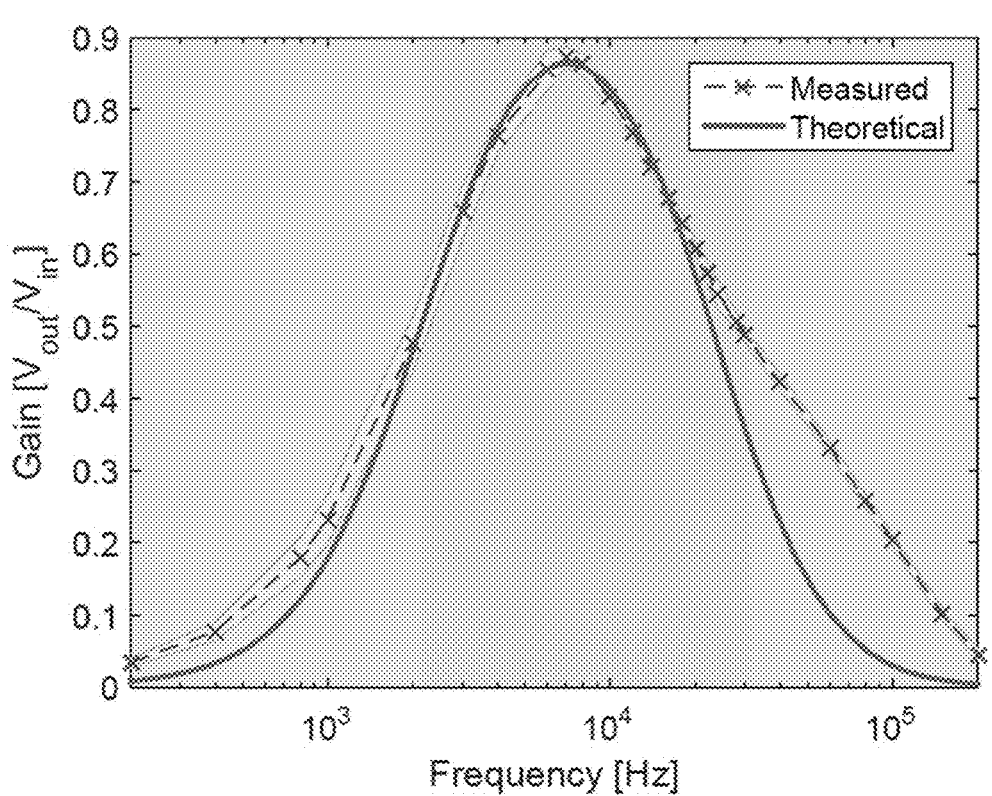
FIG. 16 plots measured filter response (plotted against the model), showing predictable behavior within the pass-band (measured Q=0:067).

The frequency response of the filtering circuitry to input sinusoids of varying frequency is shown in FIG. 16. The data is compared to a model of the theoretical behavior as given by the following transfer function:

$$F(s) = \left(\frac{s}{s+R_{f1}C_{f1}}\right)^2 \left(\frac{R_{f2}C_{f2}}{s+R_{f2}C_{f2}}\right)^2 \left(\frac{\tau_{PT}^{-1}}{s+\tau_{PT}^{-1}}\right) \quad (13)$$

Note that the transfer function also includes a term to account for the inherent low-pass filter contained in the phototransistor 22 response (characterized by the transistor rise-time, which is roughly $\tau_{PT}=15$ μS). As designed, the pass-band centers at around 8 kHz, and the data matches the model quite well near the pass-band but deviates significantly at higher frequencies. This deviation is likely due to the fact that the phototransistor 22 output no longer resembles a pure sinusoid at higher frequencies, resulting in components that cannot be filtered.

The voltage swing expected from the output of the signal conditioning circuitry is given by the following equation:

$$V_{out} = \left(1 + \frac{R_{11}}{R10}\right) i_{PT} R_8. \quad (14)$$

Figure 17:
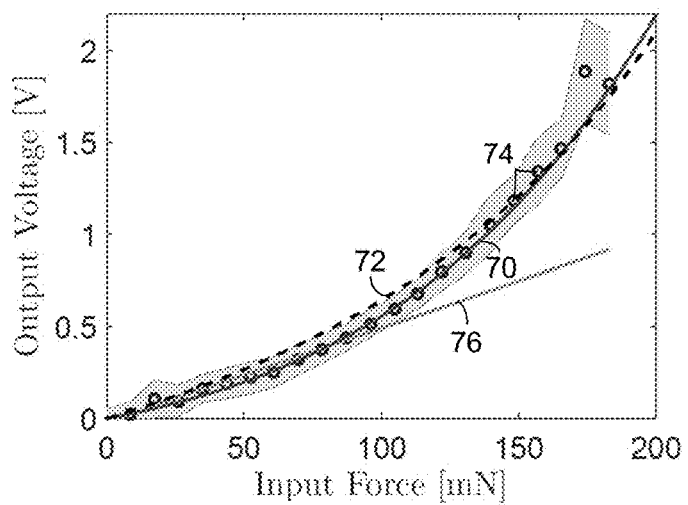
FIG. 17 plots a sensor calibration curve 70, showing a linear fit to the data 74 and a comparison to the model 72 (where the shaded area shows standard deviation of measurements).

Validation:

Sensor Calibration:

The sensor 10 was calibrated by loading the sensor 10 with a reference load-cell (LCL-005 full-bridge thin-beam load cell, Omega Engineering). The calibration curve 70 showing sensor 10 voltage output as a function of input load is shown in FIG. 17. As expected, the behavior is exponential in nature, and the model prediction 72 fits quite well with the observed results 74. Observe how the behavior is suitably approximated by a linear curve up 76 until about 100 mN of loading, as predicted by the model. The limited range is largely due to the compliance of the bias spring 18; but since the range is related to the cube of spring 18 thickness, the range/resolution can be custom-tailored by including thicker spring layers 18 in the laminate. As an example, by using 0.006-inch thick 304 stainless steel (as opposed to 0.004-inch SS) for the spring material, an overall range of around 700 mN (with a linear range of around 350 mN) can be expected.

The overall sensor 10 calibration curve is well described ($R^2=0.99$) by an exponential fit of the following form:

$$F=a\ \exp(bV_{out})+c\ \exp(dV_{out}). \quad (15)$$

For the 0-100 mN region, the behavior is suitably approximated ($R^2=0.97$) by a linear fit of the following form:

$$F|_{0-100\ mN}=mV_{out}, \quad (16)$$

where m=0.0051 V/mN. The root mean square (RMS) noise of the sensor 10, found by integrating the power spectral density of a null signal taken over 60 seconds, was found to be 1.1 mN. The resulting signal-to-noise (SNR) over the linear region (from 0 to 100 mN) is 39 dB.

Figure 18:
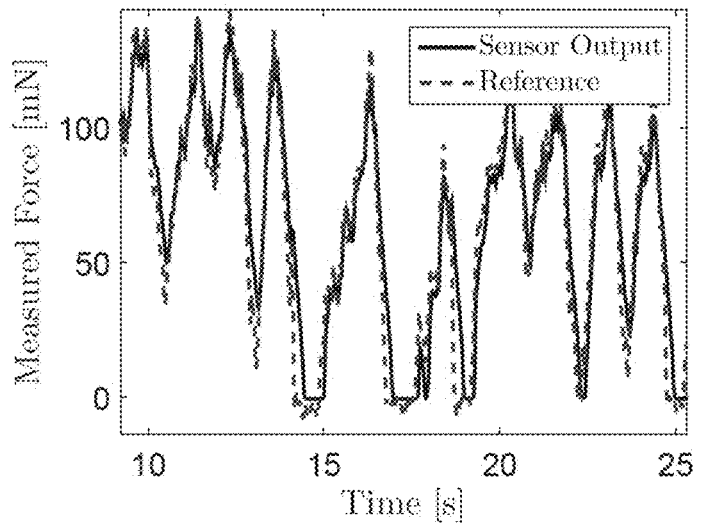
FIG. 18 plots sensor response (solid line) to a dynamic input, compared with a reference signal (dashed line) generated by a load cell.
Figure 19:
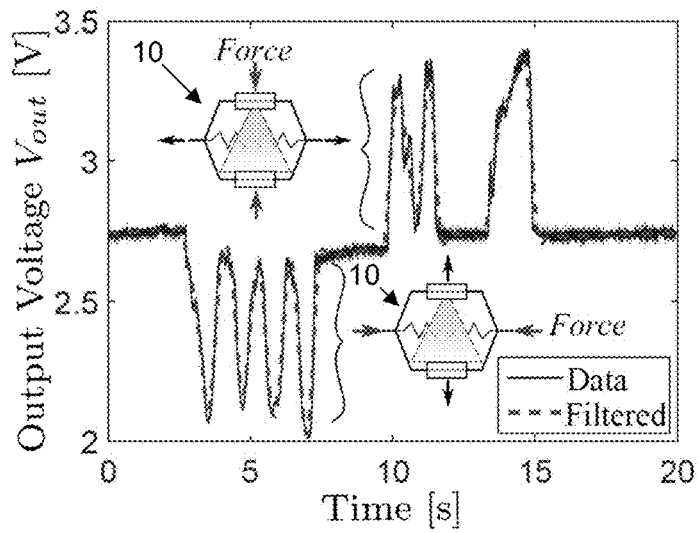
FIG. 19 plots un-calibrated data showing "multi-axis" sensing capabilities depending on sensor 10 orientation.

FIG. 18 shows the prototype sensor 10 tracking a dynamic loading profile, which is simultaneously being tracked by a reference load cell. The linear fit is being used. We see that the sensor 10 is able to accurately track the load over the input force range. FIG. 19 shows how the sensor 10 responds to different loading conditions, demonstrating flexibility in the mounting conditions and the potential for multi-axis sensing based on sensor 10 orientation.

Cannulation Simulation:

Numerous flexible/endoscope-based procedures can benefit from these distal sensing capabilities. For example, in electrograde cholangeopancreatography (ERCP), wherein the surgeon positions a catheter into the bile duct via the duodenal papilla, the surgeon relies solely on proximal haptic cues (and sporadic fluroscopic imaging) to determine whether or not he or she has successfully cannulated the bile duct. However, these forces are grossly contaminated by frictional forces within the anatomy, as well as reaction forces of the endoscope deflection plate. The papilla bifurcates into both the biliary duct and the pancreatic duct, and if the surgeon accidentally cannulates the latter, pancreatitis can occur. As such, providing gastroenterologists with a distal "sense of touch" can allow for greater awareness of the forces being exerted during cannulation.

Figure 20:
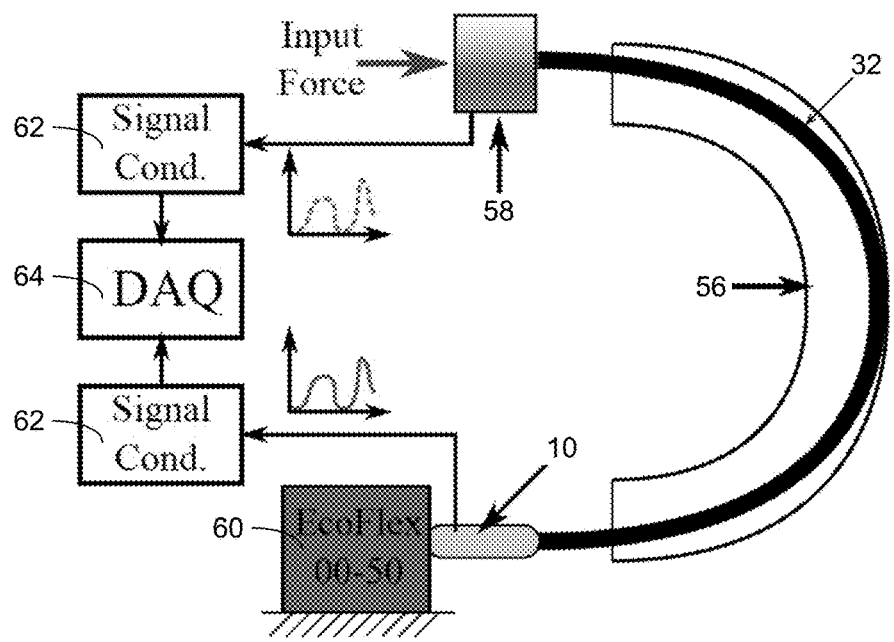
FIG. 20 schematically illustrates a sensorized catheter 32 used to probe a tissue analog through a tortuous lumen 56.

To replicate this scenario, a bench-level experiment was performed, wherein the sensorized catheter 32 was used to probe a tissue analog through a tortuous lumens 56 (simulating a gastrointestinal tract), as shown in FIG. 20. A proximal load cell 58 measures the catheter insertion forces, and the light-intensity-based sensor 10 simultaneously records interaction forces between the tip of the catheter 32 and a biological tissue analog 60 (EcoFlex 00-50 silicone rubber). Measurements from the light-intensity-based force sensor 10 and from the proximal load cell 58 are passed through respective modules for signal conditioning 62 to a data acquisition (DAQ) module 64.

Figure 21:
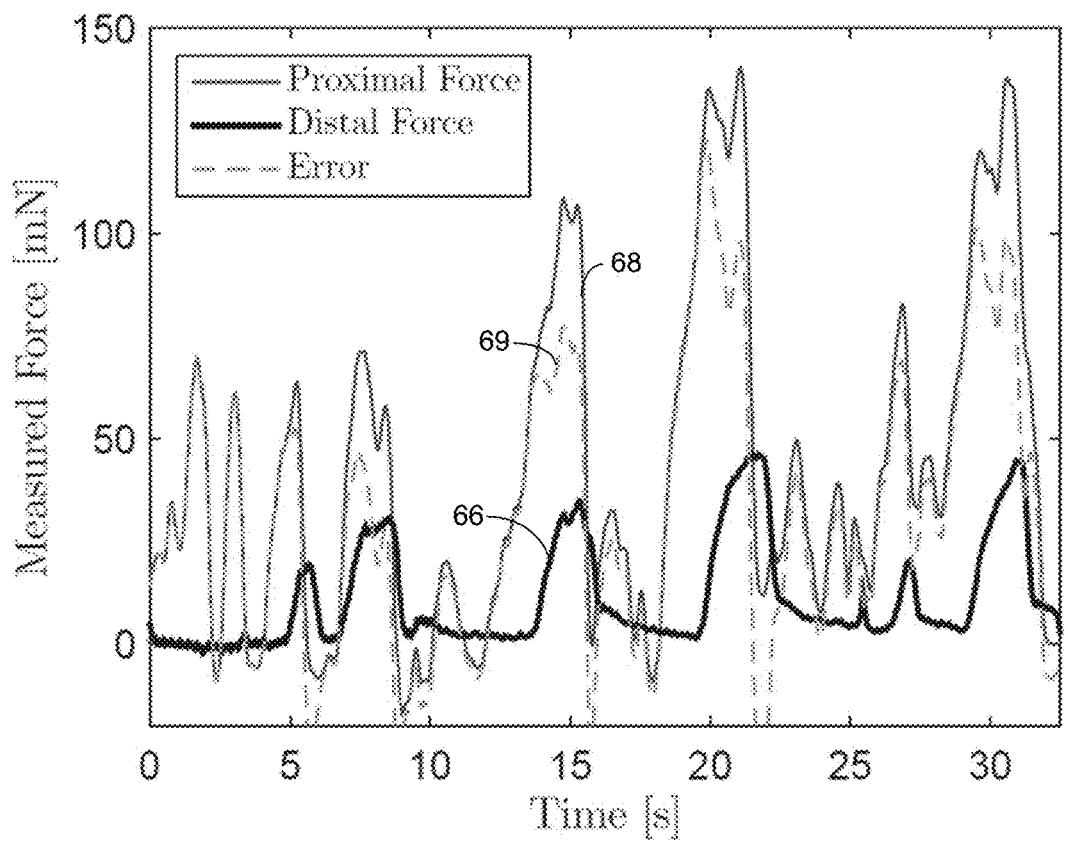
FIG. 21 plots the distal force 66 measured by the sensor 10 of the catheter shown in FIG. 20 as well as proximal force 68 measurements as a function of time.

The results are shown in FIG. 21. It is easily observed that the forces felt proximally 68 are very poorly correlated with the distal forces 66 actually being applied on the tissue and are often several times higher, as is evident from the error plotting 69. In addition, a phase delay of several seconds indicates poor system controllability. Therefore, distal sensing modalities for flexible systems are highly advantageous, as the presence of friction and lateral reaction forces along the length of the system can make it impossible to discern the actual distal force from those generated proximally.

In describing embodiments of the invention, specific terminology is used for the sake of clarity. For the purpose of description, specific terms are intended to at least include technical and functional equivalents that operate in a similar manner to accomplish a similar result. Additionally, in some instances where a particular embodiment of the invention includes a plurality of system elements or method steps, those elements or steps may be replaced with a single element or step. Likewise, a single element or step may be replaced with a plurality of elements or steps that serve the same purpose. Further, where parameters for various properties or other values are specified herein for embodiments of the invention, those parameters or values can be adjusted up or down by $1/100^{th}$, $1/50^{th}$, $1/20^{th}$, $1/10^{th}$, $1/5^{th}$, $1/3^{rd}$, $1/2$, $2/3^{rd}$, $3/4^{th}$, $4/5^{th}$, $9/10^{th}$, $19/20^{th}$, $49/50^{th}$, $99/100^{th}$, etc. (or up by a factor of 1, 2, 3, 4, 5, 6, 8, 10, 20, 50, 100, etc.), or by rounded-off approximations thereof, unless otherwise specified. Moreover, while this invention has been shown and described with references to particular embodiments thereof, those skilled in the art will understand that various substitutions and alterations in form and details may be made therein without departing from the scope of the invention. Further still, other aspects, functions, and advantages are also within the scope of the invention; and all embodiments of the invention need not necessarily achieve all of the advantages or possess all of the characteristics described above. Additionally, steps, elements and features discussed herein in connection with one embodiment can likewise be used in conjunction with other embodiments. The contents of references, including reference texts, journal articles, patents, patent applications, etc., cited throughout the text are hereby incorporated by reference in their entirety; and appropriate components, steps, and characterizations from these references may or may not be included in embodiments of this invention. Still further, the components and steps identified in the Background section are integral to this disclosure and can be used in conjunction with or substituted for components and steps described elsewhere in the disclosure within the scope of the invention. In method claims (or where methods are elsewhere recited), where stages are recited in a particular order—with or without sequenced prefacing characters added for ease of reference—the stages are not to be interpreted as being temporally limited to the order in which they are recited unless otherwise specified or implied by the terms and phrasing.

What is claimed is:

1. A light-intensity-based force sensor, comprising:
   a Sarrus linkage including:
   (a) a first plate;
   (b) a second plate; and
   (c) at least one collapsible linkage pivotably coupled to both the first plate and the second plate, wherein the collapsible linkage is configured to change a distance between the first plate and the second plate as the collapsible linkage collapses or extends along a longitudinal axis;
   a biasing mechanism coupled with the collapsible linkage to bias the collapsible linkage toward an extended configuration, wherein the first plate and the second plate are separated by a maximum distance;
   a light emitter coupled with and displaceable with the first plate; and
   a light detector coupled with and displaceable with the second plate and configured to receive light emitted from the light emitter and generate an electrical signal in response to light received from the light emitter, wherein the generated electrical signal provides an indication of the distance between the first plate and the second plate.

2. The light-intensity-based forced sensor of claim 1, wherein the Sarrus linkage, with the collapsible linkage in a collapsed state, has a height and width that are each no greater than 3 mm, wherein the height and width are orthogonal to the longitudinal axis along which the collapsible linkage extends and collapses.

3. The light-intensity-based forced sensor of claim 1, wherein the first plate, the collapsible linkage, and the biasing mechanism are configured to place the first plate at decreasing distance from the second plate as a force toward the second plate is placed upon the first plate.

4. The light-intensity-based forced sensor of claim 3, wherein the light emitter and the light detector are configured so that the light detector generates the electrical signal with an increasing intensity as the distance between the first plate and the second plate decreases.

5. The light-intensity-based forced sensor of claim 1, wherein the light-intensity-based forced sensor includes a plurality of the collapsible linkages.

6. The light-intensity-based forced sensor of claim 5, wherein each of the collapsible linkages includes an intermediate hinge midway along its length.

7. The light-intensity-based forced sensor of claim 5, wherein the biasing mechanism is a spring coupled with opposing collapsible linkages.

8. The light-intensity-based forced sensor of claim 1, wherein the light emitter is an infrared light-emitting diode.

9. The light-intensity-based forced sensor of claim 8, wherein the light detector is an infrared phototransistor.

10. The light-intensity-based forced sensor of claim 1, wherein the first plate, the second plate, and the collapsible linkage each comprise a rigid segment and a flexible layer extending from the rigid segment, wherein the flexible layer has a flexural modulus at least 5 times greater than the rigid segments; and wherein the collapsible linkage is coupled with the first and second plates via the flexible layer at gaps between the rigid segments.

11. The light-intensity-based forced sensor of claim 1, further comprising flex-circuits coupled with the light emitter and with the light detector.

12. A distal-sensing catheter, comprising:
a flexible tube including a proximal end and a distal end; and
a light-intensity-based forced sensor mounted to the distal end of the flexible tube, the light-intensity-based forced sensor comprising:
i) a Sarrus linkage including:
(a) a first plate;
(b) a second plate; and
(c) at least one collapsible linkage pivotably coupled to both the first plate and the second plate, wherein the collapsible linkage is configured to change a distance between the first plate and the second plate as the collapsible linkage collapses or extends along a longitudinal axis;
ii) a biasing mechanism coupled with the collapsible linkage to bias the collapsible linkage toward an extended configuration, wherein the first plate and the second plate are separated by a maximum distance;
iii) a light emitter coupled with and displaceable with the first plate; and
iv) a light detector coupled with and displaceable with the second plate and configured to receive light emitted from the light emitter and generate an electrical signal in response to light received from the light emitter, wherein the generated electrical signal provides an indication of the distance between the first plate and the second plate.

13. The distal-sensing catheter of claim 12, wherein the light-intensity-based forced sensor further comprises:
a computer processor in communication with the light detector; and
computer-readable memory in communication with the computer process and non-transiently storing software code for correlating light-intensity measurements from the light detector with force exerted on the first plate.

14. The distal-sensing catheter of claim 12, further comprising a power source coupled with the light emitter.

15. A method for distal light-intensity-based force sensing, the method comprising:
utilizing an elongated tool with a force sensor mounted at a distal end of the elongated tool, wherein the force sensor includes:
i) a Sarrus linkage including:
(a) a first plate;
(b) a second plate; and
(c) at least one collapsible linkage pivotably coupled to both the first plate and the second plate, wherein the collapsible linkage is configured to change a distance between the first plate and the second plate as the collapsible linkage collapses or extends along a longitudinal axis;
ii) a biasing mechanism coupled with the collapsible linkage to bias the collapsible linkage toward an extended configuration, wherein the first plate and the second plate are separated by a maximum distance;
iii) a light emitter coupled with and displaceable with the first plate; and
iv) a light detector coupled with and displaceable with the second plate and configured to receive light emitted from the light emitter and generate an electrical signal in response to light received from the light emitter, wherein the generated electrical signal provides an indication of the distance between the first plate and the second plate;
inserting the elongated tool, distal end first, into a passageway;
using the light emitter to emit light directed toward the light detector;
measuring light incidence on the light detector;
contacting at least one surface in the passageway with the first plate, wherein the contact exerts a force on the first plate that displaces the first plate toward the second plate and increases incidence of the light from the light emitter upon the light detector; and
correlating a measurement of increased light incidence measured by the light detector with the force exerted on the first plate.

16. The method of claim 15, wherein the passageway is in a human body.

17. The method of claim 16, wherein the elongated tool is an endoscope, and wherein the sensor is at a distal end of a catheter passing through a channel defined in the endoscope.

18. The method of claim 17, further comprising using the endoscope to perform an electrograde cholangeopancreatography.

* * * * *